United States Patent [19]

Gauthier-Lafaye et al.

[11] Patent Number: 4,619,791

[45] Date of Patent: Oct. 28, 1986

[54] CARBONYLATION OF METHYL ACETATE TO ACETIC ANHYDRIDE

[75] Inventors: Jean Gauthier-Lafaye, Lyons; Robert Perron, Charly, both of France

[73] Assignee: Rhone-Poulenc Chimie De Base, Courbevoie, France

[21] Appl. No.: 435,752

[22] Filed: Oct. 21, 1982

[30] Foreign Application Priority Data

Oct. 21, 1981 [FR] France ................ 81 20007

[51] Int. Cl.$^4$ ............................................. C07C 51/56
[52] U.S. Cl. .................................................. 260/549
[58] Field of Search ................................ 260/549, 546

[56] References Cited

U.S. PATENT DOCUMENTS 4,234,504 11/1980 Hallgren et al. ............... 260/463
4,239,698 12/1980 Isshiki et al. .................... 260/549
4,353,844 10/1982 Gauthier-Lafaye et al. ....... 260/549

FOREIGN PATENT DOCUMENTS 1538782 1/1979 United Kingdom .

OTHER PUBLICATIONS

Cooper, Mervyn K. et al., *Chemical Abstracts*, vol. 95 (1981), #53061p.
Shell International Research Maatschappij, *Chemical Abstracts*, vol. 95 (1981), #149,909x.

*Primary Examiner*—Natalie Trousof
*Assistant Examiner*—L. Hendriksen
*Attorney, Agent, or Firm*—Burns, Doane, Swecker & Mathis

[57] ABSTRACT

Methyl acetate is carbonylated to acetic anhydride with carbon monoxide, in liquid phase, in an anhydrous reaction medium, in the presence of a catalytically effective amount of (i) nickel, (ii) methyl iodide, (iii) an alkali metal iodide, and (iv) a crown ether.

21 Claims, No Drawings

CARBONYLATION OF METHYL ACETATE TO ACETIC ANHYDRIDE

SUMMARY OF THE INVENTION

The present invention relates to the preparation of acetic anhydride by the carbonylation of methyl acetate, and, more especially, to the preparation of acetic anhydride by the carbonylation of methyl acetate in an anhydrous reaction medium, in the liquid phase, in the presence of a catalytically effective amount of (i) nickel, (ii) methyl iodide, (iii) an alkali metal iodide and (iv) a crown ether.

DETAILED DESCRIPTION OF THE INVENTION

More particularly according to this invention, the subject process requires the presence of a catalytically effective amount of nickel. Any source of nickel can be used within the scope of the present invention. The nickel can be introduced in the metallic state (for example, Raney nickel) or in any other convenient form. Exemplary of nickel compounds which are suitable for carrying out the subject process, representative are: nickel carbonate, oxide, hydroxide, halides, in particular the iodide, and carboxylates, in particular the acetate.

Nevertheless, when a nickel salt is introduced, a longer or shorter reaction induction period may be observed and it may therefore be preferred to use compounds of nickel zero, such as nickel tetracarbonyl and bis-(triphenylphosphine)nickel dicarbonyl. Of course, one skilled in the art will readily appreciate which appropriate forms of the nickel compounds will suffice, and will of course ensure that the precise form in which the nickel is introduced into the reaction medium is not of fundamental importance, in particular in the context of a continuous process.

Too, the amount of nickel introduced is not critical. The proportion of nickel, which influences the reaction rate, is determined according to the reaction rate which is considered suitable, taking account of the other reaction parameters. In general, an amount ranging from 5 to 2,000 milligram atoms of nickel per liter of solution affords satisfactory results. The reaction is preferably carried out with a proportion ranging from 20 to 1,000 milligram atoms of nickel per liter of solution.

To carry out the present invention, methyl iodide must also be present in the reaction medium. It is not necessary to introduce this particular component of the catalyst system at the beginning of the reaction, and it is possible to use, for example, free iodine, hydriodic acid, an alkyl iodide which is different from methyl iodide, or an acyl iodide. As would also be readily apparent to the skilled artisan, iodine and the aforesaid types of iodine compounds can be considered as precursors of, and in situ form methyl iodide in the subject reaction.

In general, the methyl iodide is present in the reaction medium in an amount ranging from 1 to 100 mols, and preferably in an amount ranging from 5 to 50 mols, per gram atom of nickel present in the said medium.

The catalyst system employed within the scope of the present invention also comprises an alkali metal iodide. The use of sodium iodide or potassium iodide is preferred.

In general, the alkali metal iodide is used in an amount ranging from 0.2 to 50 mols per gram atom of nickel present in the reaction medium; it is preferred to use from 0.5 to 20 mols of alkali metal iodide per gram atom of nickel and more preferably from 1 to 10 mols per gram atom of nickel.

The catalyst system employed within the scope of the present invention also comprises a crown ether. These compounds are macrocyclic polyethers, which are themselves known to the prior art and which can be represented by the following formulae (I) to (III):

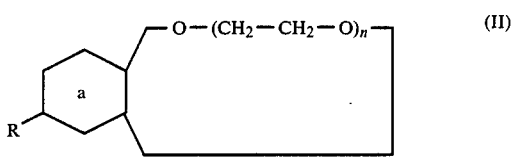

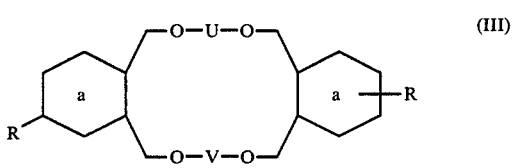

in which m and n are integers such that the macrocyclic rings contain from 3 to 20 oxygen atoms; a is a phenylene, cyclohexylene or 2,3-naphthylene radical; R is an alkyl radical having at most 4 carbon atoms, or a hydrogen radical; and U and V, which are identical or different, are each a radical of the formula:

in which p is an integer which can be zero and is such that the ring contains at most 20 oxygen atoms, and q is an integer ranging form 1 to 10, q preferably being equal to 2 if p is other than zero.

For further information relating, in particular, to the preparation of such crown ethers, reference is made to the following literature:

(1) *Journal of the Chemical Society*, Volume 89, pages 7,017 et seq. (1967);

(2) *Chemical Reviews*, Volume 74, No. 3, pages 351 et seq. (1974).

Exemplary of the crown ethers which are suitable for carrying out the present invention, representative are: 12-crown-4, 15-crown-5, 18-crown-6, 21-crown-7, 24-crown-8, benzo-9-crown-3, benzo-12-crown-4, benzo-15-crown-5, benzo-18-crown-6, (t-butylbenzo)-15-crown-5, (t-butylbenzo)-18-crown-6, cyclohexyl-12-crown-4, cyclohexyl-15-crown-5, cyclohexyl-18-crown-6, (tert.-butylcyclohexyl)-15-crown-5, (tert.-butylcyclohexyl)-18-crown-6, (2,3-naphtho)-15-crown-5, (2,3-naphtho)-18-crown-6, dibenzo-14-crown-4, dibenzo-15-crown-5, dibenzo-16-crown-5, dibenzo-18-crown-6, dibenzo-21-crown-7, dibenzo-24-crown-8, dibenzo-30-crown-10, dibenzo-60-crown-20, di-(tert.-butylbenzo)-18-crown-6, di-(2,3-naphtho)-18-crown-6, dicyclohexyl-18-crown-6, di-(tert.-butylcyclohexyl)-18-crown-6, dicyclohexyl-24-crown-8, dicyclohexyl-30-crown-10 and dicyclohexyl-60-crown-20.

Preferably, the macrocyclic polyethers of the formulae I to III above which contain from 5 to 10 oxygen atoms in the ring will be used. Among the polyethers of the formula III, those in which U and V are identical, q is equal to 2, p is an integer equal to 1, 2 or 3 and R represents hydrogen will preferably be selected.

15-Crown-5 and 18-crown-6 are more particularly suitable for carrying out the subject process.

The amount of crown ether to be used can vary over wide limits. No advantage is observed when more than one mol of crown ether is used per mol of alkali metal iodide. In general, the amount of crown ether is at least 1 to 5 mol % relative to the alkali metal iodide. The optimum amount of crown ether to be used will depend largely on the nature and amount of the alkali metal iodide used and also on the nature of the crown ether itself. It is generally on the order of 10 to 75 mol % relative to the alkali metal iodide.

According to a particularly advantageous embodiment of the present invention, the catalyst system also contains an alkaline earth metal salt or, preferably, a lithium salt.

The precise nature of the anion of this salt is not of fundamental importance, and examples which are representative of salts which can be used within the scope of the invention are: hydroxides, chlorides, bromides, iodides, carbonates and nitrates, and also carboxylates containing at most 12 carbon atoms.

Among the aforesaid salts, lithium iodide, carbonate and carboxylates are particularly suitable for carrying out the present invention. It is preferred to use a lithium carboxylate having at most 5 carbon atoms, lithium acetate proving particularly effective.

In general, one (or more) lithium, magnesium or calcium salt is used in an amount such that the atomic ratio of the metal (M) to the nickel ranges from 1 to 100, although it is possible to use smaller or larger amounts. Good results are obtained with an atomic ratio M/Ni ranging from 2 to 25.

The catalyst system heretofore described is particularly effective for the preparation of acetic anhydride by the carbonylation of methyl acetate in the liquid phase.

As mentioned above, the reaction is carried out in the liquid phase, under a pressure above atmospheric pressure. In general, the reaction is carried out under a total pressure of more than 15 bars; there is no advantage in using a pressure of as much as 700 bars. To carry out the process according to the invention satisfactorily, a total pressure of 25 to 200 bars is recommended.

The reaction temperature is generally above 140° C., although it is not necessary to use a temperature as high as 300° C. Good results are obtained within the temperature range from 160° to 220° C.

The carbon monoxide used for the carbonylation is preferably employed in essentially pure form, such as is available commercially. However, the presence of impurities, such as carbon dioxide, oxygen, methane and nitrogen, can be tolerated. The presence of hydrogen is not harmful, even in relatively large proportions.

Upon completion of the reaction, the acetic anhydride obtained is separated from the other constituents of the reaction medium by any suitable means, for example, by distillation.

In order to further illustrate the present invention and the advantages thereof, the following specific examples are given, it being understood that same are intended only as illustrative and in nowise limitative. In said examples to follow, RY (%) denotes the number of mols of acetic anhydride produced per 100 mols of methyl acetate introduced.

EXAMPLE 1

25 ml of methyl acetate, 20 ml of acetic anhydride, 8 millimols of nickel tetracarbonyl, 80 millimols of methyl iodide, 100 millimols of sodium iodide and 20 millimols of 15-crown-5 were introduced into a Hastelloy B 2 autoclave having a capacity of 125 ml. After the autoclave had been closed, a pressure of 40 bars of carbon monoxide was established therein. Shaking by means of a reciprocating system was commenced and the autoclave was heated to 180° C., over the course of about 20 minutes, by means of an annular furnace. The pressure in the autoclave was then 64 bars; it was subsequently maintained constant and equal to 70 bars by successively introducing additional amounts of carbon monoxide.

After a reaction time of 3 hours at 180° C., the shaking and heating were stopped; the autoclave was cooled and degassed. The reaction mixture was then analyzed. 79 g/hour×liter of acetic anhydride were obtained: RY (%)=38.

Control experiment (a)

Example 1 was repeated, but without introducing the crown ether. After 2 hours at 180° C., no reaction was observed.

EXAMPLE 2

25 ml of methyl acetate, 20 ml of acetic anhydride, 8 millimols of nickel tetracarbonyl, 79 millimols of methyl iodide, 100 millimols of potassium iodide and 20 millimols of 18-crown-6 were introduced into a Hastelloy B 2 autoclave having a capacity of 125 ml. After the autoclave had been closed, a pressure of 40 bars of carbon monoxide was established thereon. Shaking by means of reciprocating system was commenced and the autoclave was heated to 180° C., over the course of about 20 minutes, by means of an annular furnace. The pressure in the autoclave was then 64 bars; it was subsequently maintained constant and equal to 70 bars by successively adding additional amounts of carbon monoxide.

After a reaction time of 2 hours at 180° C., the shaking and heating were stopped; the autoclave was cooled and degassed. The reaction mixture was then analyzed. 40 g/hour×liter of acetic anhydride were obtained: RY (%)=15.

EXAMPLE 3

25 ml of methyl acetate, 20 ml of acetic anhydride, 8 millimols of nickel tetracarbonyl, 80 millimols of methyl iodide, 100 millimols of sodium iodide, 20 millimols of 15-crown-5 and 40 millimols of lithium acetate were introduced into a Hastelloy B 2 autoclave having a capacity of 125 ml. After the autoclave had been closed, a pressure of 40 bars of carbon monoxide was established therein. Shaking by means of a reciprocating system was commenced and the autoclave was heated to 180° C., over the course of about 20 minutes, by means of an annular furnace. The pressure in the autoclave was then 64 bars; it was subsequently maintained constant and equal to 70 bars by successively introducing additional amounts of carbon monoxide.

After a reaction time of 2 hours at 180° C., the shaking and heating were stopped; the autoclave was cooled and degassed. The reaction mixture was then analyzed. 135 g/hour×liter of acetic anhydride were obtained: RY (%)=36.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of acetic anhydride, comprising carbonylating methyl acetate with carbon monoxide, in liquid phase, in an essentially anhydrous reaction medium, in the presence of a catalytically effective amount of (i) nickel, (ii) methyl iodide, (iii) an alkali metal iodide, and (iv) a crown ether.

2. The process as defined by claim 1, the total reaction pressure ranging from 15 to 700 bars.

3. The process as defined by claim 2, the reaction temperature ranging from 140° to 300° C.

4. The process as defined by claim 1, the concentration of the nickel (i) ranging from 5 to 2,000 milligram atoms per liter of reaction medium.

5. The process as defined by claim 4, the concentration of the nickel (i) ranging from 20 to 1,000 milligram atoms per liter of reaction solution.

6. The process as defined by claim 4, the crown ether (iv) comprising a macrocyclic polyether having one of the following formulae (I) to (III):

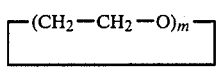  (I)

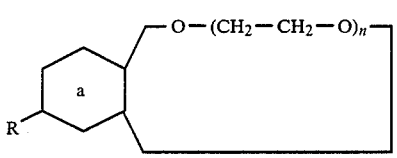  (II)

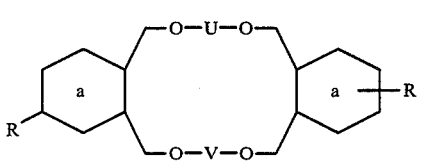  (III)

in which m and n are integers such that the macrocyclic rings contain from 3 to 20 oxygen atoms; a is a phenylene, cyclohexylene or 2,3-naphthylene radical; R is hydrogen or an alkyl radical having up to 4 carbon atoms; and U and V, which are identical or different, are each a radical of the formula:

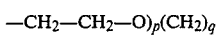  (IV)

in which p is an integer which can be zero and is such that the ring contains at most 20 oxygen atoms, and q is an integer ranging from 1 to 10.

7. The process as defined by claim 6, wherein the radicals having the formula (IV), q is 2 and p is other than zero.

8. The process as defined by claim 6, said crown ether (iv) having from 5 to 10 ring oxygen atoms.

9. The process as defined by claim 6, said crown ether (iv) having the formula (III):

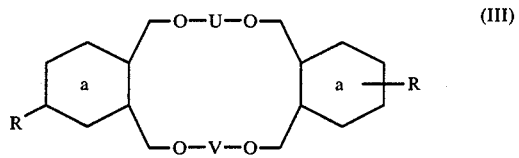  (III)

in which a is a phenylene, cyclohexylene or 2,3-naphthylene radical; R is hydrogen; and U and V, which are identical, are each a radical of the formula:

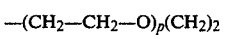

in which p is equal to 1, 2 or 3.

10. The process as defined by claim 6, said crown ether (iv) comprising 15-crown-5 or 18-crown-6.

11. The process as defined by claim 6, wherein the methyl iodide (ii) is present in the reaction medium in an amount ranging from 1 to 100 mols per gram atom of nickel.

12. The process as defined by claim 11, said alkali metal iodide (iii) comprising sodium iodide or potassium iodide.

13. The process as defined by claim 11, wherein the alkali metal iodide (iii) is present in the reaction medium in an amount ranging from 0.2 to 50 mols per gram atom of nickel.

14. The process as defined by claim 13, wherein the amount of the crown ether (iv) present in the reaction medium comprises at least 5 mol % of the alkali metal iodide (iii).

15. The process as defined by claim 14, wherein the amount of the crown ether (iv) present in the reaction medium comprises at most one mol per mol of the alkali metal iodide (iii).

16. The process as defined by claim 15, wherein the amount of the crown ether (iv) present in the reaction medium comprises from 10 to 50 mol % of the alkali metal iodide (iii).

17. The process as defined by claim 13, the reaction medium further comprising (v) an alkaline earth metal or lithium salt.

18. The process as defined by claim 17, said salt (v) comprising a lithium carboxylate having up to 12 carbon atoms.

19. The process as defined by claim 18, said lithium salt (v) comprising lithium acetate.

20. A composition of matter comprising a catalytically effective amount of (i) nickel, (ii) methyl iodide, (iii) an alkali metal iodide, and (iv) a crown ether.

21. The composition of matter as defined by claim 20, further comprising (v) an alkaline earth metal or lithium salt.

* * * * *